United States Patent
Wessman et al.

(10) Patent No.: US 6,952,616 B2
(45) Date of Patent: Oct. 4, 2005

(54) MEDICAL LEAD AND METHOD FOR ELECTRODE ATTACHMENT

(75) Inventors: Bradley J. Wessman, Maple Grove, MN (US); Peter J. Pohndorf, Stillwater, MN (US)

(73) Assignee: MicroNet Medical, Inc., White Bear Lake, MN (US)

( * ) Notice: Subject to any disclaimer, the term of this patent is extended or adjusted under 35 U.S.C. 154(b) by 227 days.

(21) Appl. No.: 09/822,728

(22) Filed: Mar. 30, 2001

(65) Prior Publication Data

US 2002/0038139 A1 Mar. 28, 2002

Related U.S. Application Data

(63) Continuation-in-part of application No. 09/670,062, filed on Sep. 26, 2000.

(51) Int. Cl.[7] ............................................. A61N 1/05
(52) U.S. Cl. ............................................. 607/122
(58) Field of Search ........................... 600/373, 377, 600/393, 395; 607/116–119, 122

(56) References Cited

U.S. PATENT DOCUMENTS

| | | | |
|---|---|---|---|
| 4,280,511 A | 7/1981 | O'Neill | 128/784 |
| 4,355,646 A * | 10/1982 | Kallok et al. | 128/786 |
| 4,381,014 A | 4/1983 | Sandstrom et al. | 128/786 |
| 4,432,377 A | 2/1984 | Dickhudt | 128/786 |
| 4,437,474 A | 3/1984 | Peers-Trevarton | |
| 4,444,195 A | 4/1984 | Gold | |
| 4,559,951 A | 12/1985 | Dahl et al. | |
| 4,566,467 A | 1/1986 | DeHaan | 128/784 |
| 4,590,950 A | 5/1986 | Iwaszkiewicz et al. | 128/786 |
| 4,592,372 A | 6/1986 | Beranek | 128/786 |
| 4,614,395 A | 9/1986 | Peers-Trevarton | 339/97 |
| 4,706,682 A | 11/1987 | Stypulkowski et al. | 128/642 |
| 4,764,324 A | 8/1988 | Burnham | |
| 4,848,352 A | 7/1989 | Pohndorf et al. | |
| 4,890,623 A | 1/1990 | Cook et al. | |
| 4,934,049 A | 6/1990 | Kiekhafer et al. | |
| 4,944,088 A | 7/1990 | Doan et al. | 29/858 |
| 5,016,646 A | 5/1991 | Gotthardt et al. | 128/784 |
| 5,040,544 A | 8/1991 | Lessar et al. | |
| 5,118,400 A | 6/1992 | Wollam | |
| 5,178,957 A | 1/1993 | Kolpe et al. | |
| 5,251,643 A | 10/1993 | Osypka | |
| 5,324,322 A | 6/1994 | Grill, Jr. et al. | |
| 5,350,404 A * | 9/1994 | Adams et al. | 607/5 |
| 5,374,285 A | 12/1994 | Vaiani et al. | |
| 5,417,208 A * | 5/1995 | Winkler | 128/642 |
| 5,431,681 A | 7/1995 | Helland | 607/4 |
| 5,433,742 A | 7/1995 | Willis | |
| 5,458,629 A | 10/1995 | Baudino et al. | 607/116 |
| 5,582,609 A | 12/1996 | Swanson et al. | |
| 5,609,622 A | 3/1997 | Soukup et al. | 607/122 |
| 5,712,462 A * | 1/1998 | Berkowitz et al. | 219/117.1 |
| 5,788,692 A | 8/1998 | Campbell et al. | |
| 5,796,044 A | 8/1998 | Cobian et al. | |
| RE35,924 E | 10/1998 | Winkler | 600/373 |
| 5,928,277 A | 7/1999 | Laske et al. | |
| 6,018,684 A | 1/2000 | Bartig et al. | |
| 6,151,520 A | 11/2000 | Combs | |
| 6,208,881 B1 | 3/2001 | Champeau | |
| 6,253,111 B1 | 6/2001 | Carner | |
| 6,324,415 B1 | 11/2001 | Spehr et al. | |

* cited by examiner

*Primary Examiner*—Jeffrey R. Jastrzab
*Assistant Examiner*—Frances P. Oropeza
(74) *Attorney, Agent, or Firm*—Peter R. Lando

(57) ABSTRACT

The present invention provides a medical lead for implantation within a patient. The medical lead has a seem-less lead body having one or more electrodes secured to the distal end and one or more connector bands attached to the proximal end of the lead.

15 Claims, 6 Drawing Sheets

MEDICAL LEAD AND METHOD FOR ELECTRODE ATTACHMENT

CROSS-REFERENCE TO RELATED APPLICATIONS

This is a continuation-in-part of co-pending application Ser. No. 09/670,062, filed Sep. 26, 2000.

BACKGROUND OF THE INVENTION

1. Field of the Invention

The present invention relates to a medical leads and particularly to medical leads having unitary construction.

2. Description of the Related Art

Implantable leads form an electrical connection between a pulse generator or other electronic device and a tissue or structure in the body. For example, leads transmit electric signals used to stimulate cardiac or nerve tissue in one direction and signals generated by sensors placed in proximity to particular organs or tissues in the opposite direction. Leads typically include one or more electrodes at the lead's distal end. The electrodes are designed to form an electrical connection with a tissue or organ. In addition, most leads also include a lead connector at the lead body's proximal end. Lead connectors are adapted to electrically and mechanically connect leads to the pulse generators or other electronic medical devices. A conductor connects the electrode to the lead connector. Commonly, the conductor takes the form of a single or multifilar wire coil. Although, there is an increasing interest in using stranded cables as conductors. Regardless of the conductor's form, an insulating material typically surrounds the conductors. Spinal chord stimulation leads are typically formed with individually insulated conductors surrounded by a separate lead body tube. Together, the conductor and the insulating material form the lead body. The lead body couples the lead connector at the proximal end with the electrode at the distal end.

Present lead designs frequently electrically connect a separate electrode assembly to the distal end of the lead. This results in an electrical connection and a seam between the electrode assembly and the lead body. Other current lead designs add ring electrodes over the lead body's distal end. To access the wound conductors within the lead body, the conductors are pulled from the lead body for welding to the edge of the ring electrode. The removal of the conductors from the lead body may result in a breach of the lead body's insulator that must later be sealed creating a seam. These seams and other junctions provide a potential point for failure and the potential for electrical leakage. Therefore, a need exists for a lead having a seam-less or unitary construction.

Similar to electrode assemblies, present lead designs frequently couple a separate connector assembly to the proximal end of the lead. Again, the produces a seam between the connector and the lead body. Other connector designs may add ring electrodes over the lead body's proximal end. To access the wound conductors within the lead body, the conductors are pulled from the lead body for welding to the edge of the ring electrode. The removal of the conductors from the lead body may result in a breach of the lead body's insulator that must later be sealed creating a seam. Again, These seams and other junctions provide a potential point for failure and the potential for electrical leakage. Therefore, a need exists for a lead having a unitary construction.

Further, manufacturing leads is costly. A significant portion of the cost is allocated to electrically connecting the conductors to the various electrodes, sensors and connectors used in the industry. Forming a secure electrical junction has proven difficult and time consuming. Laser welds are commonly used to connect the conductors to the electrodes. The conductors are typically helically wound into a coil for increased reliability and flexibility. Band electrodes are typically connected to conductors by welding in an operation separate from the application of the lead body tube. Once the band electrodes are connected to the conductors, an extruded tube is placed over the conductor coil and welded band electrodes are connected to the lead body tube by insert molding or RF welding. Band electrodes may also be connected to a conductor by etching away a region of insulator, applying a coating of electrically conductive adhesive, and then placing the band electrode around the conductor. This etching method is complex, not amenable to automation, and expensive. Therefore, a need exists for a method that reduces complexity and is easily automated to reduce production costs.

In another method of attachment, band electrodes are electrically connected to coiled conductors by placing a soft metal in a hole cut into an insulating sleeve. An electrode is placed over the metal and crimped or swaged to bring the electrode, soft metal and coiled conductors into electrical contact and to secure the electrode the lead body. The crimping or swaging method of connection results in electrical connections between the conductor and the band electrode that may fail. Further, swaging to electrically connect an electrode to a conductor is time consuming and difficult to implement with the modern reduced diameter leads. Hence, a need exists for an improved manufacturing technique to secure band electrodes to conductors that reduces the time, complexity and cost while increasing reliability.

In addition, current manufacturing techniques frequently require adding elements, such as collars, when connecting a band electrode to a coil. The added elements increase the lead's diameter near the weld. In application, a uniform diameter weld would result in a smaller lead. A smaller diameter lead is desired to allow placement in restricted spaces such as the epidural space or cardiac veins to reduce the effects of implanted lead on the patient. Further, a smaller lead allows for a smaller introducer that reduces the trauma associated with implantation and similarly a smaller removal sheath when explanting the lead. Hence, there exists a need to reduce the diameter of the welds used to secure electrodes to conductors in implantable medical leads.

The present invention meets the above-referenced needs and provides other advantages and improvements that will be evident to those skilled in the

SUMMARY OF THE INVENTION

The present invention provides a medical lead having a novel seam-less design which electrically connects the electrodes, connectors and/or sensors to the conductors through the insulator of the lead body. A medical lead in accordance with the present invention includes a lead body, at least one band electrode and at least one band conductor. The lead body extends the length of the lead and includes a seamless insulator between the proximal and distal ends of the lead insulating at least one conductor within the lead body. At least one band electrode and at least one band connector are secured between the proximal and distal end of the lead body and electrically connected to the conductor. Typically, the band connector is positioned adjacent the proximal end of the lead body and the band electrode is positioned adjacent the distal end of the lead body. Further, the band electrode and the band connector may be electrically connected to the conductor by welding to a conductive pad within a welding region.

DETAILED DESCRIPTION OF THE INVENTION

Figure 1:
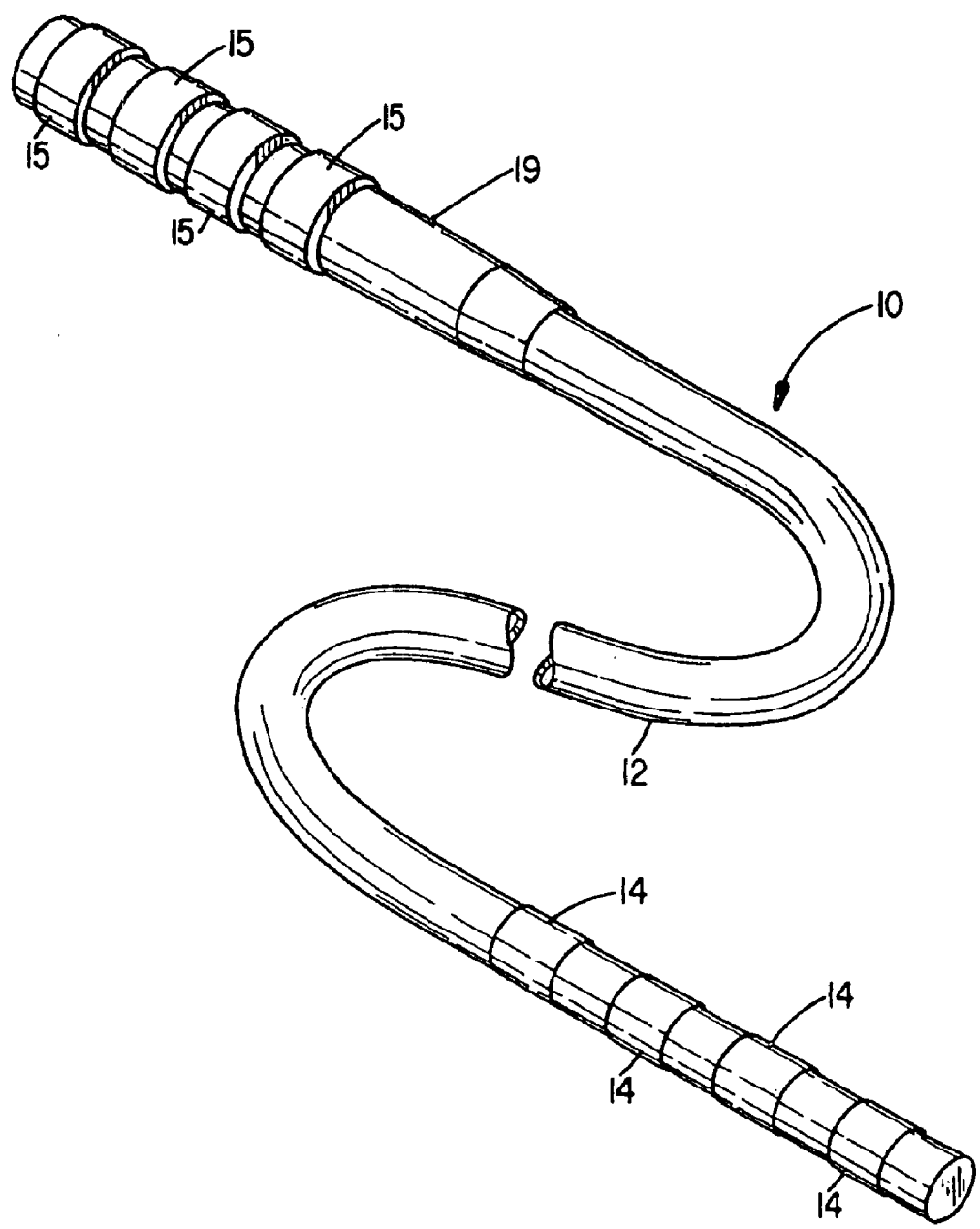
FIG. 1 illustrates a perspective view of a lead in accordance with the present invention.

The present invention provides a medical lead and a method for lead manufacture. The invention is described generally in the context of a neurostimulating lead and a method for manufacturing a neurostimulating lead as a specific example for illustrative purpose only. The appended claims are not intended to be limited to any specific example or embodiment described in this patent. It will be understood by those skilled in the art that leads in accordance with the present invention may be used for a wide variety of applications including, but not limited to, leads and catheters for use with cardiac monitoring devices, neurostimulating devices, neuromonitoring devices or other medical devices using leads or catheters. Further, in the drawings described below, the reference numerals are generally repeated where identical elements appear in more than one figure.

FIG. 1 illustrates an embodiment of a seam-less lead 10 in accordance with the present invention. Leads designed for neurostimulation typically have two or more longitudinally spaced band electrode 14 and the lead's distal end and an equivalent number of band connectors 15 at the proximal end to connect the lead to the particularly medical device. Lead 10 includes a lead body 12, four band electrodes 14 and four connector bands 15, for exemplary purposes. Connector bands 15 are shown disposed about a sleeve 19 secured over the lead body to increase the diameter allowing insertion of a reduced diameter lead's connector into a standard connector port of a medical device. Typically, one or more band electrode 14 and one or more band connectors 15 are provided. Lead 10 is generally configured to transmit an electric signal from a pulse generator (not shown) to a spinal nerve or peripheral nerve. Thus, band electrodes 14 are typically located at the distal end of lead 10. Lead body 12 includes flexible lead insulator surrounding one or more conductors. The conductors are electrically coupled to band electrodes 14 at the distal end and band connectors 15 at the proximal end of lead 10.

Typically, lead body 12 is flexible, elastomeric structure having a round cross-section. Alternatively, lead body's cross-section could be any number of shapes appropriate for the specific application. The diameter of lead body 12 may vary between the proximal end and distal end of lead 10. Depending on the particular application, the diameter of lead body 12 may be smaller than 2 French for neurological and myocardial mapping/ablation leads and can be sizes larger than 12 French for other applications. The lead insulator is generally configured to insulate the conductors and to present a smooth biocompatible external surface to body tissues and form a continuous and seam-less structure between the proximal and distal ends of lead 10. When a plurality of conductors form a multipolar lead, individual conductors are typical electrically isolated from one another within the insulator. The insulator material is typically selected based on biocompatibility, biostability and durability for the particular application. The insulator material may be silicone, polyurethane, polyethylene, polyimide, polyvinylchloride, PTFE, ETFE, or other materials known to those skilled in the art. Moreover, alloys and blends of these materials may also be formulated to control the relative flexibility, torqueability, and pushability of the lead.

The conductors 22 may take the form of solid wires, drawn-filled-tube (DFT), drawn-brazed-strand (DBS), stranded cables or other forms that will be recognized by those skilled in the art. The conductors may be composed of stainless steel, MP35N, or other conductive materials known to those skilled in the art. The number, size, and composition of the conductors will depend on particular application for the lead.

At least one band electrode 14 is positioned at the distal end of lead body 12 to electrically contact a target tissue or organ and at least one band connector 15 is positioned at the proximal end of lead body 12 to electrically connect the conductors to the neurostimulator. The band electrodes 14 and band connectors 15 are typically made of a conductive material such as platinum, gold, silver, platinum-iridium, stainless steel, MP35N or other conductive metals or alloys thereof known to those skilled in the art. Band electrodes 14 and band connectors 15 typically composed of a material thin enough to allow for welding of the elements to the underlying conductive pad, as discussed below. For neurostimulation, band electrodes 14 are typically between 1 and 10 millimeters long and have a diameter between about 2 and about 8 French but are more typically between 4 and 6 French. Typically, band connections 15 have a size and configuration appropriate to connect the lead to a particular neurostimulator.

Figure 2:
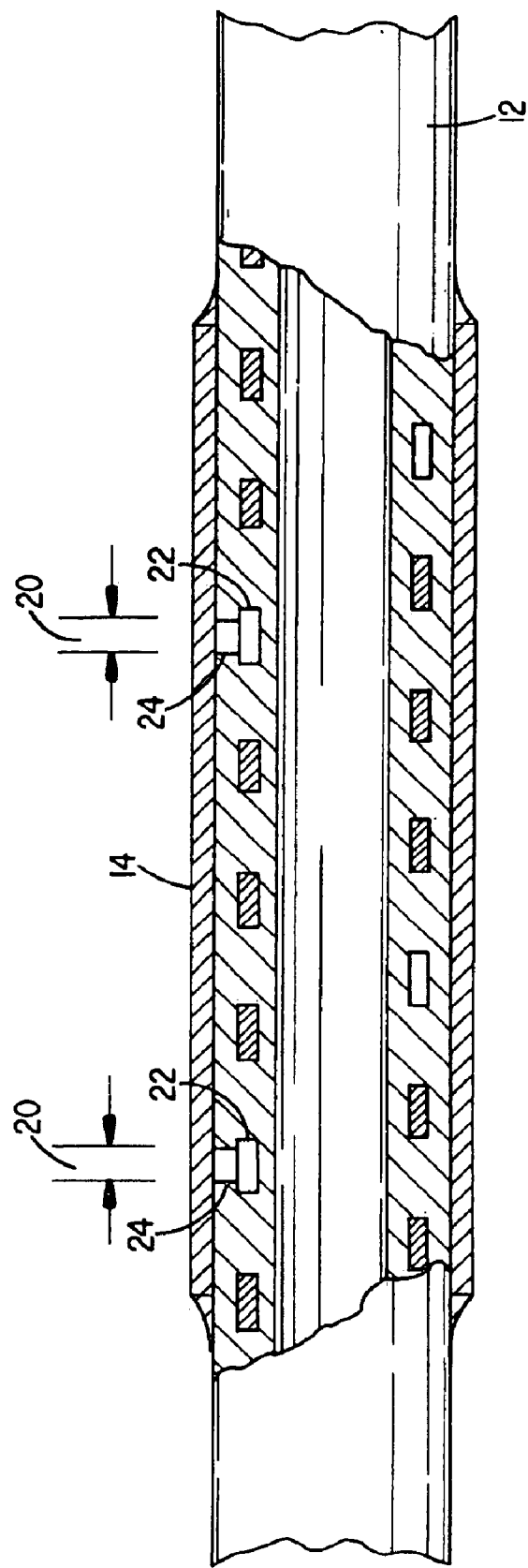
FIG. 2 illustrates a longitudinal cross-sectional view of a of a lead showing an embodiment of the connection between a coiled conductor and a band with a conductive pad.

FIG. 2 illustrates the details of an embodiment of the connection between a conductor 22 and band electrode 14 in accordance with the present invention. For purpose of the following description band electrodes 14 and band connectors 15 should be considered synonymous and band electrode 14 will be used throughout the remainder of the description. Band electrode 14 is disposed about lead body. Lead body 12 is shown with four spirally wound conductors 22 connected at two locations to band electrode 14. Band electrode 14 is connected lead body 12 at welding regions 20 by a weld through band electrode 14 to electrically connect the band to conductive pad 24. The distal end and proximal end of band electrode 14 are positioned to extend over welding regions 20. Band electrode 14 is connected to the same conductor 22 twice for exemplary purpose. A single band may be connected to multiple conductors if desired.

Figure 3:
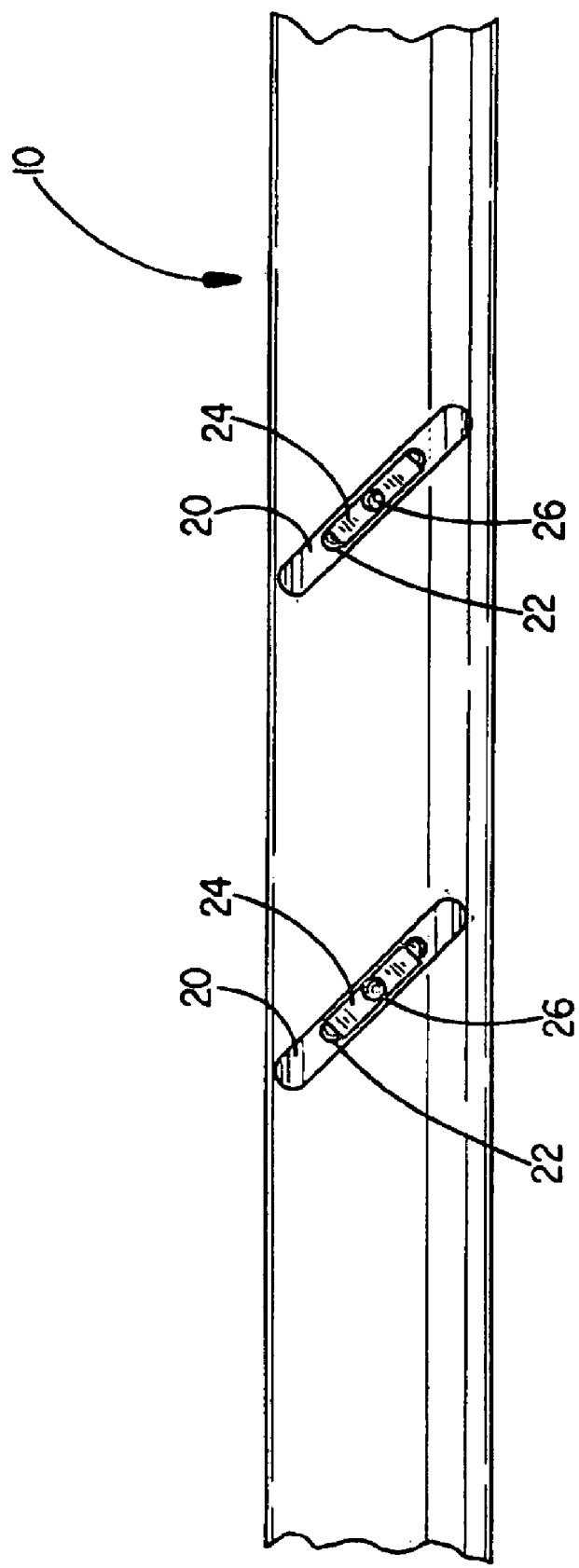
FIG. 3 illustrates a top view of a lead, as shown in FIG. 2, without the band.

FIG. 3 illustrates a top view of a lead body having the insulating material removed to form welding region 20 by exposing conductor 22. Welding region 20 provides access to conductor(s) 22 for electrically connecting band electrode 14 to conductor 22. Welding region 20 is typically formed by removing the insulating material from lead body 10. The insulating material is removed to expose small sections of the individual conductors 22 without breaching an inner lumen, if present. Typically, an excimer laser is used to remove the insulating material. When the insulator is removed by laser, welding region 20 may be in the form of a groove in the insulator. Alternatively, welding region 20 may take a variety of forms and orientations that expose a sufficient surface area of conductor 22 to form an electrical connection with a conductive pad, discussed below. When in the form of a groove, welding region 20 is typically formed such that the groove runs parallel to conductor 22. Regardless of the form of welding region 20, sufficient surface area of conductor 22 is exposed to secure a conductive pad 22 or an elongated conductive element 34, shown in FIG. 4, to conductor 22.

Referring to FIGS. 2 and 3, a conductive pad 24 is positioned within welding region 20 during manufacture to facilitate the electrical connection of band electrode 14 and conductor 22. Conductive pad 24 may be formed by centering a length of wire or other piece of material over the welding region and melting the wire or material at a point over the welding region 20. As the material melts, the ends of the wire are drawn into the welding region to form the conductive pad. A weld 26 is typically used to secure the conductive pad 24 in electrical contact with conductor 22. Alternatively, conductive pad 24 may be secured using an adhesive. Conductive pad 22 may be composed of any of a variety of conductive materials that can be welded or secured with adhesives. Some suitable metals include stainless steel, MP35N, Pt-Ir, platinum, silver, gold, copper, vanadium or other metal that will be recognized by one skilled in the art upon review of this disclosure. Conductive pad 24 is positioned within welding region 20 so that conductive pad 24 is in electrical contact with conductor 22. Typically, conductive pad is welded to the conductor prior to placing band electrode 14 over the welding regions and conductive pads 24. A pulsed Neodymium:yttrium-arsenic-garnet (YAG) laser may be used to weld conductive pad 24 to conductor 22. FIG. 2 shows a side view of a cross-section of two grooves 20 that expose two regions of the same conductor 22. Conductive pads 24 are welded to conductor 22 within grooves 20. Band electrode 14 is placed over lead body 12 of lead 10 and welded to conductive pads 24, thereby securing band electrode 14 to lead body 12 and electrically connecting conductor 22 and band electrode 14. Band electrode 14 may be further secured to lead body 12 by swaging, crimping and/or adhesives. Alternatively, the band electrode may be secured to the lead body by heating the lead body. Heating the lead body stress-relieves the plastic increasing the outside diameter and securing the band electrode over the lead body. In addition, heating the lead body may be used to create a lead having a uniform diameter between band electrode 14 and lead body 12.

Figure 4:
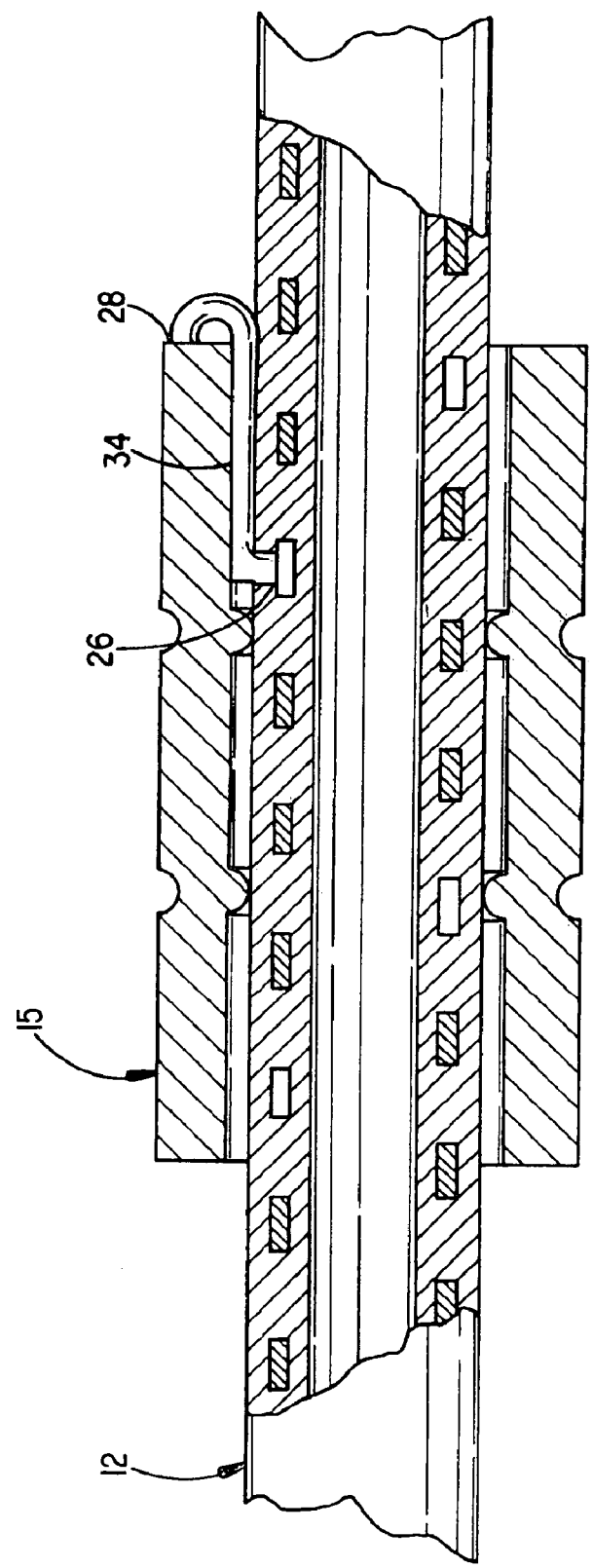
FIG. 4 illustrates a longitudinal cross-sectional view of a of a lead showing the connection between a coiled conductor and a band with an elongated conductive element.
Figure 5:
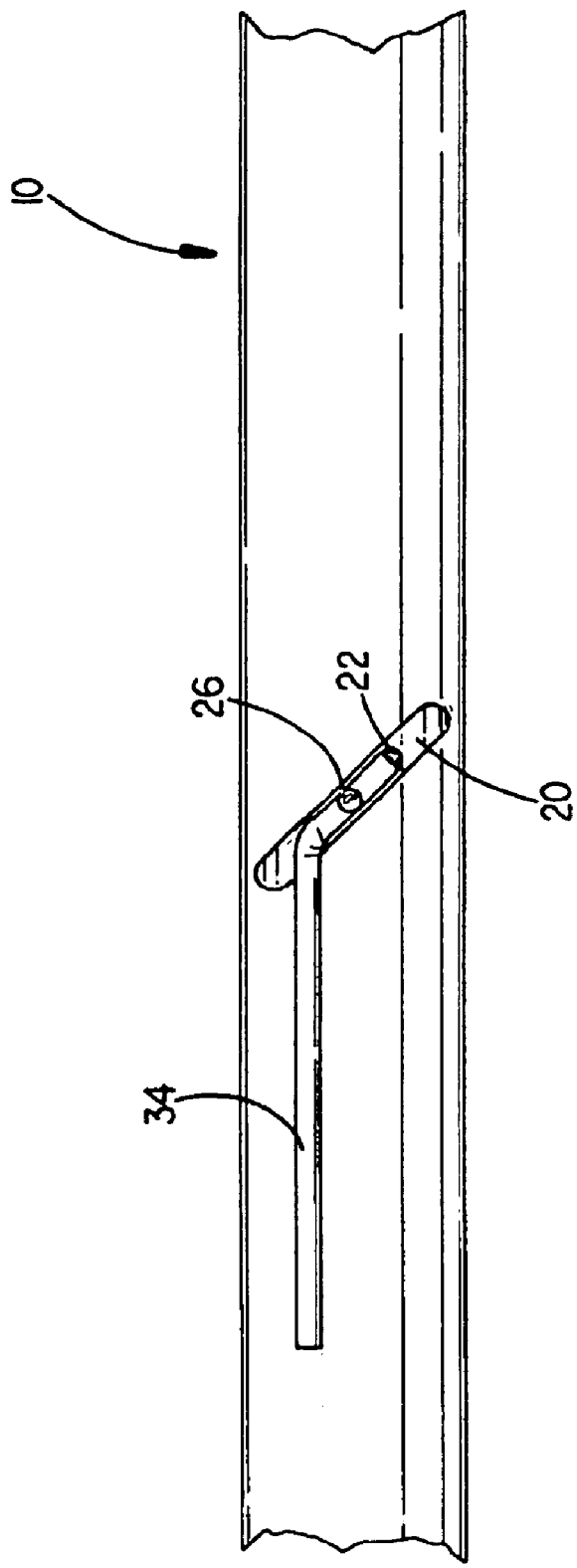
FIG. 5 illustrates a top view of a lead, as shown in FIG. 4, without the band.

FIGS. 4 and 5 illustrate the details of another embodiment of a connection between conductor 22 and a band electrode 14 in accordance with the present invention. In the embodiments shown in FIGS. 4 and 5, an elongated conductive element 34 is used to electrically connect band electrode 14 to conductor 22. The elongated conductive element may be in the form of a wire, a ribbon wire, or a cable. The metal may be stainless steel, MP35N, Pt—Ir, platinum, silver, gold, copper, vanadium or other metal that will be recognized by one skilled in the art upon review of this disclosure. A distal end of elongated conductive element 34 is electrically connected to band electrode 14. Typically, the electrical connection employs a weld 28, although a conductive adhesive or other method or conductively attaching may be used. FIG. 4 shows a longitudinal cross-section of a lead body having four spirally wound conductors. One or more welding regions 20 are formed through the insulating material by removing the insulating material from lead body 10. Typically, the insulating material is removed with a laser. The proximal end of elongated conductive element 34 is positioned within welding region 20 so that the proximal end is in electrical contact with conductor 22. Typically, the proximal end is secured to conductor 22 prior to placing band electrode 14 over lead body 12. Again, the proximal end is typically welded although a conductive adhesive or other method of conductively attaching the proximal end may be used. The elongated conductive element 34 and attached proximal end are typically configured to allow band electrode 14 to pass over elongated conductive element 34 during assembly. The distal ends of elongated conductive elements 34 may then be electrically connected to band electrode 14.

FIGS. 4 and 5 illustrate a single exemplary connection between conductor 22 and band electrode 14 by welds 26 and 28. Thus, FIG. 4 shows only one groove 20 exposing conductor 22. The proximal end of elongated conductive element 24 is positioned within groove 20 is welded to conductor 22. Band electrode 14 is placed over lead body 12 and welded to elongated conductive element 34, thereby electrically connecting conductor 22 and band electrode 14. Band electrode 14 may be further secured to lead body 12 by swaging, crimping, adhesives and/or insert molding. In addition, swaging may reduce the outside diameter of band electrode 14 to permit the manufacture of a lead of uniform diameter. Alternatively, lead body 12 may be expanded by heating to create a uniform diameter between band electrode 14 and lead body 12.

Figure 6A:
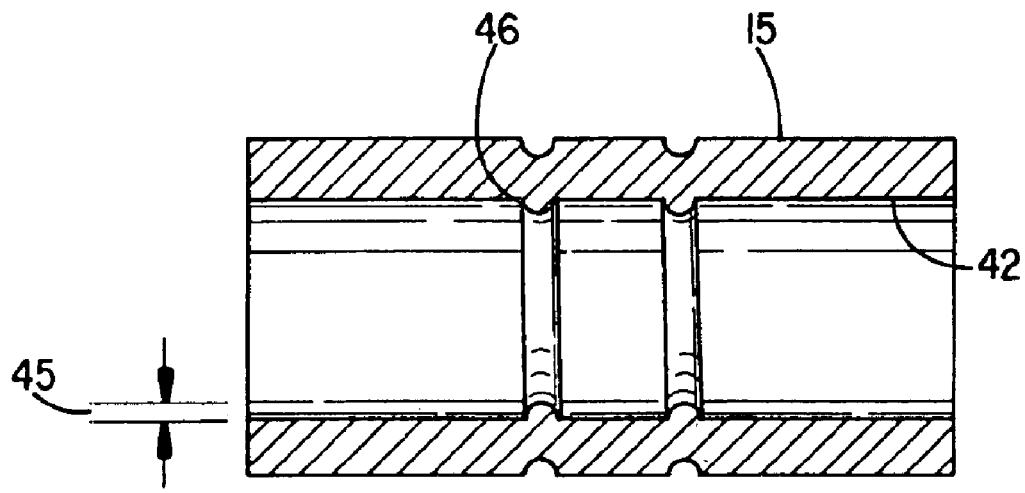
FIG. 6A illustrates a cross-sectional longitudinal view of a band electrode, as shown in FIGS. 4 and 5.
Figure 6B:
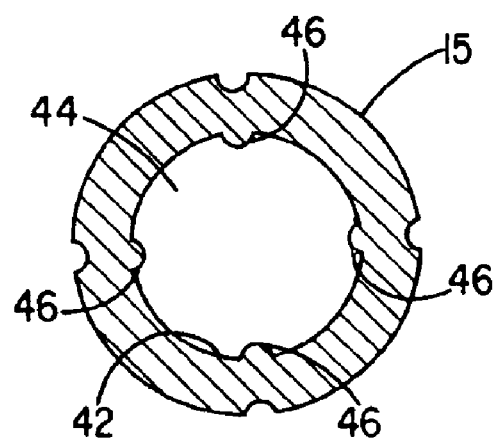
FIG. 6B illustrates and end view of the band electrode, as in FIG. 6A.

FIGS. 6A and 6B illustrate a novel embodiment of band electrode 14 which may be used in conjunction with the present invention. Band electrode 14 includes an inner wall 42 defining a lumen 44. At least one projection 46 is formed on the inner wall 42. Projections 46 define a space between inner wall 42 and an outer surface of the lead body during assembly. Projections 46 may be molded on the inner surface; formed by crimping the exterior surface of the band; or added as separate elements secured to the inner surface of the band. Projections 46 have a height 45 which defines the amount of space between the outer surface of the lead body and inner wall 42. Height 45 is generally selected to allow conductive pads 24 and/or conductive elements 34 to pass beneath the inner wall during assembly. Typically, three projections are provided at positions around the circumference of band electrode 14 to center band electrode 14 over lead body 12 during assembly. Centering band electrode 14 so that height 45 is substantially the same around the circumference of the lead body assures clearance of the conductive element during assembly.

What is claimed is:

1. A medical lead, comprising:
    a lead body having an insulator and having at least one conductor, and wherein the insulator comprises,
        a first region formed by removal of at least a portion of the insulator, the first region exposing at least a portion of the at least one conductor, and
        a second region formed by removal of at least a portion of the insulator, the second region exposing at least a portion of the at least one conductor;
    a first conductive pad positioned within the first region and electrically connected to the at least one conductor;
    a second conductive pad positioned within the second region and electrically connected to the at least one conductor; and at least one electrode welded to the first conductive pad and welded to the second conductive pad to electrically connect the at least one electrode to the at least one conductor through the first region and to the at least one conductor through the second region.

2. The medical lead in accordance with claim 1 wherein the lead body further comprises a distal end and a proximal end, and the first region, the second region and the at least one electrode are located proximate the distal end of the lead body.

3. The medical lead in accordance with claim 2 wherein the insulator further comprises, a third region formed by removal of at least a portion of the insulator, the third region exposing at least a portion of the at least one conductor, and a fourth region formed by removal of at least a portion of the insulator, the fourth region exposing at least a portion of the at least one conductor; and wherein the lead further comprises, a third conductive pad positioned within the third region and electrically connected to the at least one conductor;

a fourth conductive pad positioned within the third region and electrically connected to the at least one conductor; and a second electrode welded to the third conductive pad and welded to the fourth conductive pad to electrically connect the second electrode to the at least one conductor through the third region and to the at least one conductor through the fourth region; and wherein the third region, the fourth region and the second electrode are located proximate the proximal end of the lead body.

4. The medical lead in accordance with claim 1 wherein the lead body further comprises:

a second conductor;

and wherein the insulator further comprises, a third region formed by removal of at least a portion of the insulator, the third region exposing at least a portion of the second conductor, and a fourth region formed by removal of at least a portion of the insulator, the fourth region exposing at least a portion of the second conductor; and a third conductive pad positioned within the third region and electrically connected to the second conductor;

a fourth conductive pad positioned within the fourth region and electrically connected to the second conductor; and a second electrode welded to the first conductive pad and welded to the second conductive pad to electrically connect the at least one electrode to the second conductor through the third region and to the second conductor through the fourth region.

5. The medical lead in accordance with claim 4 wherein the lead body further comprises a distal end and a proximal end, and the first region, the second region and the at least one electrode are located proximate the distal end of the lead body.

6. The medical lead in accordance with claim 5 wherein the third region, the fourth region and the second electrode are located proximate the distal end of the lead body.

7. A medical lead, comprising:

a lead body having an insulator and at least one conductor, wherein the insulator comprises, a first welding region formed by removal of at least a first portion of the insulator from the lead body, at least a portion of the first welding region formed to expose at least a first portion of the at least one conductor, and a second welding region formed by removal of at least a second portion of the insulator from the lead body, at least a portion of the second welding region formed to expose at least a second portion of the at least one conductor;

a first conductive element having at least a portion thereof positioned within the first welding region, the first conductive element welded to the at least one conductor;

a second conductive element positioned within the second welding region, the second conductive element welded to the at least one conductor; and a band electrically connected to the first conductive element and electrically connected to the second conductive element.

8. The medical lead in accordance with claim 7 wherein the band is welded to the first conductive element and welded to the second conductive element.

9. The medical lead in accordance with claim 8 wherein the first welding region comprises a first groove cut in the insulator, and the second welding region comprises a second groove cut in the insulator.

10. The medical lead in accordance with claim 7 wherein the band is electrically connected to the first conductive element using a conductive adhesive.

11. A medical lead, comprising:

a lead body having an insulator and at least one conductor, wherein the insulator comprises, a first welding region formed by removal of at least a first portion of the insulator from the lead body, at least a portion of the first welding region formed to expose at least a first portion of the at least one conductor, and a second welding region formed by removal of at least a second portion of the insulator from the lead body, at least a portion of the second welding region formed to expose at least a second portion of the at least one conductor;

a first conductive pad within the first welding region, the first conductive pad electrically connected to the at least one conductor;

a second conductive pad within the second welding region, the second conductive pad electrically connected to the at least one conductor; and a band welded to the first conductive pad at the first welding region to electrically connect the band to the at least one conductor, and welded to the second conductive pad at the second welding region to electrically connect the band to the at least one conductor.

12. The medical lead in accordance with claim 11 wherein the first welding region comprises a first groove cut in the insulator, and the second welding region comprises a second groove cut in the insulator.

13. The medical lead in accordance with claim 12 wherein the first groove and the second groove run parallel to the at least one conductor.

14. The medical lead in accordance with claim 11 wherein the first conductive pad is electrically connected to the at least one conductor using a weld, and the second conductive pad is electrically connected to the at least one conductor using a weld.

15. The medical lead in accordance with claim 11 wherein each of the first welding region, the second welding region, the first conductive pad, the second conductive pad, and the band are positioned proximate a distal end of the lead body, and wherein the insulator positioned proximate a proximal end of the lead body further comprises a third welding region formed by removal of at least a third portion of the insulator from the lead body, at least a portion of the third welding region formed to expose at least a third portion of the at least one conductor, and the lead body further comprises:

a third conductive pad within the third welding region, the third conductive pad electrically connected to the at least one conductor; and a second band welded to the third conductive pad at the third welding region to electrically connect the second band to the at least one conductor.

* * * * *